United States Patent
Ferrier et al.

(10) Patent No.: US 6,562,757 B1
(45) Date of Patent: May 13, 2003

(54) PLANT-PROTECTION TREATMENT OF PLANTS AND COMPOSITIONS WHICH CAN BE USED FOR THIS PURPOSE

(75) Inventors: Frederic Ferrier, Marseilles (FR); Edwige Le Bras, Marseilles (FR); Georges Ramel, deceased, late of Rognac (FR), by Marie-Lise Jacqueline Brigitte Pailleret, legal representative; Gerard Joncheray, Vernon (FR)

(73) Assignee: Cerexagri S.A., Plaisir (FR)

( * ) Notice: Subject to any disclaimer, the term of this patent is extended or adjusted under 35 U.S.C. 154(b) by 0 days.

(21) Appl. No.: 09/558,388

(22) Filed: Apr. 26, 2000

(30) Foreign Application Priority Data

Apr. 26, 1999 (FR) .............................................. 99 05236

(51) Int. Cl.⁷ .......................... A01N 57/00; A01N 37/00
(52) U.S. Cl. ........................................ 504/127; 504/142
(58) Field of Search ........................ 424/600; 504/127, 504/142

(56) References Cited

FOREIGN PATENT DOCUMENTS

| | | | |
|---|---|---|---|
| EP | 0 007 307 A1 | 12/1978 | ...................... 11/4 |
| EP | 0 565 262 A1 | 3/1993 | ...................... 37/4 |
| EP | 0 766 919 A1 | 10/1996 | ...................... 59/20 |
| FR | 0 739 256 | 10/1995 | ...................... 59/20 |
| GB | 2 333 707 A | 8/1999 | |
| HU | 48438 | 6/1989 | |
| IL | 97676 | * 10/1994 | |
| JP | 55-27164 | 1/1978 | ...................... 59/6 |
| JP | 55-27164 | 2/1980 | |
| WO | WO 91/13552 | 3/1991 | ...................... 59/20 |
| WO | WO 94/24225 | 4/1994 | ...................... 15/2 |

OTHER PUBLICATIONS

Copy of European Search Report dated Jul. 5, 2000.

French Search Report.

* cited by examiner

*Primary Examiner*—Alton Pryor
(74) *Attorney, Agent, or Firm*—Smith, Gambrell & Russell, LLP

(57) ABSTRACT

To increase the effectiveness of a cupric plant-protection composition and therefore to reduce the dose of copper used per hectare, a copper source, in non-chelated form, is combined with a sparingly soluble calcium and/or zinc and/or manganese chelate. This combination makes it possible to obtain, in situ, the gradual release of a soluble copper chelate.

16 Claims, No Drawings

PLANT-PROTECTION TREATMENT OF PLANTS AND COMPOSITIONS WHICH CAN BE USED FOR THIS PURPOSE

FIELD OF THE INVENTION

The present invention relates to the plant-protection field and has more particularly as subject the antifungal treatment of crops, as well as cupric compositions which can be used in this treatment.

BACKGROUND OF THE INVENTION

Cultivated plants are subject to many diseases due in particular to phytopathogenic fungi, the most well known of which is *Plasmopara viticola,* which is responsible for grape downy mildew.

The means for combating these parasites involve various types of compositions which may be classified in two main categories:

cupric compositions, the active principle of which is the copper ion $Cu^{2+}$;

synthetic organic products, the activity of which is not directly related to the presence of $Cu^{2+}$ copper ions.

The role of the $Cu^{2+}$ copper ions as means for protecting against diseases caused by phytopathogenic fungi has been known for a long time. Thus, for example, copper sulphate is known to be a very good fungicide but it is highly phytotoxic, due to its acidity and to its high solubility in water, where all the copper is found in the form of aqueous cupric ions ($Cu^{2+}$(aq)).

In order to overcome this problem of phytotoxicity, the use of copper sulphate alone has been replaced by that which makes use of its neutralized form, it being possible for this neutralization to be carried out with an alkaline agent, such as, for example, calcium hydroxide or sodium hydroxide.

One of these neutralized forms, which has been used for a very long time and is still being used, is the result of an aqueous mixture of copper sulphate and lime, a mixture which is better known under the name of Bordeaux mixture.

Other conventional-type cupric compositions which are also used in this field are, for example, copper oxychloride, copper hydroxide, copper carbonate and cuprous oxide.

These conventional cupric fungicides are generally formulated in the form of aqueous suspension or soluble concentrates, dispersible granules or wettable powders.

They are generally used in the proportion of 3000 g of copper metal equivalent per 200 liters of water and per hectare, by spraying over the plants to be protected (foliage, stem, fruits).

Cupric fungicides, such as Bordeaux mixture, copper oxychloride, copper hydroxide, copper carbonate and cuprous oxide, are complexes which are very slightly soluble in water at neutral pH. The amount of soluble aqueous copper ($Cu^{2+}$(aq)) released by these is of the order of a few ppm (1 to 10 mg/l) at pH 7, but this very small amount of $Cu^{2+}$(aq) copper is sufficient to ensure the antifungal activity with respect to phytopathogenic fungi such as *Plasmopara viticola.*

However, despite their fungicidal effectiveness, conventional cupric fungicides exhibit three major disadvantages:

the non-control of the amount of $Cu^{2+}$(aq) active principle released after application, the disappearance of a portion or of all of the antifungal activity of $Cu^{2+}$(aq) by formation of complexes with some biological molecules (in particular thiols) present at the surface of the leaf, partial coverage of the plant, the extent of which varies according to the fineness of the product.

Despite good neutralization of the cupric compound and of its formulation, the amount of aqueous copper released can vary substantially and can cause phytotoxicity. This is because the amount of $Cu^{2+}$(aq) copper released from the solid composition deposited on the leaves during spraying changes in a way which cannot be predicted as a function of the variation in the various factors of the environment in the region of the solid. These factors are, for example, ambient humidity, dissolved carbon dioxide gas, the temperature and the presence of certain plant and/or microorganic exudates, such as acetic acid. The amount of $Cu^{2+}$(aq) can thus change, for example, from a few ppm to more than 100 ppm, resulting in a risk of phytotoxicity. Although Bordeaux mixture is the cupric compound which is the least sensitive to these variations, the equilibrium between optimum fungicidal effect and phytotoxicity, a function of the amount of $Cu^{2+}$(aq) selectively released into the microenvironment, nevertheless remains uncontrollable with conventional cupric compounds.

Their second disadvantage lies in the complexing of $Cu^{2+}$(aq) by certain plant and/or microorganic exudates which render non-bioavailable, and therefore inactive against the pathogenic agent, a portion of the active material ($Cu^{2+}$(aq)) resulting from the cupric compound. Some molecules belonging to the group of the thiols can thus remove a portion of the active material ($Cu^{2+}$(aq)) by precipitation. Some of the effectiveness of the conventional cupric compound is thus lost.

Finally, the cupric particles constituting the reservoir of $Cu^{2+}$(aq) ion are partially lost by mechanical entrainment (leaching) when it rains, despite an appropriate adherent-type formulation and/or the use of a Bordeaux mixture as cupric compound, the latter being recognized as the most adherent to foliage in comparison with other conventional cupric compounds. This phenomenon increases in importance as the acidity of the environment increases.

The result of these disadvantages is that, on the one hand, the quality of the fungicidal protection provided by the cupric compounds varies with environmental factors and that, on the other hand, the total amount of copper sprayed per hectare is greater than the minimum amount of copper needed in bioavailable form. This necessitates the use of a minimum dose of 3000 g/ha of copper metal to ensure good fungicidal protection.

DETAILED DESCRIPTION OF THE INVENTION

The aim of the invention is thus to overcome these disadvantages and to provide cupric plant-protection compositions which correspond better to the requirements of maximum effectiveness with lower doses of copper per hectare (in comparison with the use of conventional cupric products), while not exhibiting the risk of phytotoxicity or while reducing it.

It is known, from Patent Application WO 91/13552, that the presence of certain copper chelates, such as copper citrate or copper malate, makes it possible to increase the fungicidal protection. However, these copper chelates exhibit the disadvantage of being very soluble and thus completely leachable, which does not make possible lasting protection against the pathogenic agent.

It has now been found that sparingly soluble calcium, zinc or manganese chelates, in combination with a conventional cupric fungicide constituting a source of $Cu^{2+}$ ions, make it possible to obtain in situ (on the plant) the gradual release of the corresponding copper chelate.

The main subject of the invention is therefore a process for the plant-protection treatment of plants, characterized in that it consists in combining a copper source, in non-chelated form, and a sparingly soluble calcium and/or zinc and/or manganese chelate in order to obtain, in situ, the gradual release of a soluble copper chelate.

Another subject of the invention is a plant-protection composition comprising a copper source, in non-chelated form, and at least one chelate of an α-hydroxycarboxylic, diphosphonic, polyphosphonic or α-hydroxyphosphonic acid and of calcium and/or of zinc and/or of manganese.

In the process and the plant-protection composition according to the invention, the copper source, in non-chelated form, is advantageously chosen from conventional cupric compounds, such as, for example, Bordeaux mixture, copper hydroxide, copper oxychloride, copper carbonate, cuprous oxide and copper hydroxide sulphates (brochantite, posnjakite, antlerite).

According to a preferred embodiment of the present invention, use is made, as copper source, of a Bordeaux mixture in accordance with Patent FR 2,739,256, the contents of which are incorporated here by way of reference. In the Bordeaux mixture in accordance with the abovementioned patent, virtually all the copper is in the brochantite state and, in the dry state, it does not comprise more than 20% by weight of bassanite. Such a Bordeaux mixture can be obtained by reacting an aqueous copper sulphate solution and an aqueous lime suspension in a $Ca(OH)_2/CuSO_4$ molar ratio of between 0.60 and 0.75 (preferably between 0.65 and 0.70 approximately) at a temperature ranging from ambient temperature to 90° C. (preferably between approximately 40 and 70° C.) and for a time sufficient to convert virtually all the copper complexes to brochantite. The reaction product exists in the form of a more or less concentrated aqueous suspension which does not comprise bassanite and which, optionally after concentrating in the form of a paste (for example by centrifuging), can be used directly in the manufacture of fungicidal formulations of SC type (liquid suspension concentrates) or of WG type (water-dispersible granules). In the manufacture of wettable powders of the WP type, the paste obtained after concentrating is dried under conditions such that the content of bassanite in the dry product does not exceed 20%; this content can be easily monitored by analysis of the copper assay of the dry product, which must not exceed 27.3% by weight.

The expression "calcium and/or zinc and/or manganese chelate" is understood here to mean any compound or mixture of compounds exhibiting the element or elements calcium and/or zinc and/or manganese chelated by at least one α-hydroxycarboxylic, diphosphonic, polyphosphonic or α-hydroxyphosphonic acid, with or without neutralization of the acid functional groups by an alkaline agent.

Mention may be made, as examples of α-hydroxycarboxylic acids, of citric, glycolic, tartronic, gluconic, lactic, malic, tartaric and saccharic acids, it being possible for the final five to be in the L or D or DL form.

Mention may be made, as examples of phosphonic or α-hydroxyphosphonic acids, of nitrilotris(methylenephosphonic), ethylenediaminetetrakis (methylenephosphonic), hexamethylenediaminetetrakis(methylenephosphonic), diethylenetriaminepentakis(methylenephosphonic) and 1-hydroxyethane-1,1diphosphonic acids.

In the context of the present invention, the solubility in water of the calcium and/or zinc and/or manganese chelate to be used can range from 0.001 to 50 g/l at ambient temperature. The choice will advantageously be made of a chelate with a solubility of between 0.01 and 5 g/l.

The amount of calcium and/or zinc and/or manganese chelate in the composition according to the invention must be sufficient to gradually chelate and dissolve at least a portion of the $Cu^{2+}$ ions present in the copper source.

Use will generally be made, in the compositions according to the invention, of a chelate/copper molar ratio of between 0.005 and 10, preferably of between 0.01 and 5 and, more preferentially, of between 0.05 and 1.

The compositions according to the invention can be presented in the form of suspensions, of wettable powders, of dustable powders or of dispersible granules. Generally, the presence of a calcium, zinc or manganese chelate in the plant-protection compositions does not in any way prevent the latter from being able to be formulated using adjuvants commonly used by the person skilled in the art (surface-active agents, antifoaming agents, inert fillers, and the like) and from also being able to comprise conventional organic fungicides.

It has been possible to demonstrate the notable effectiveness of the compositions according to the invention in a wide pH range (2.5 to 12), in particular in neutral or alkaline medium, where the copper is not in the $Cu^{2+}(aq)$ form but is bonded to the chelate in question while remaining soluble. It is, however, recommended to adjust the pH of the compositions so that, after dilution and during application, the pH is between 5.0 and 9.0 and more particularly between 6.0 and 9.0, so as to avoid, during application, phytotoxicity or a depressive effect on the plant due to an excessively acidic or excessively alkaline pH. Moreover, the joint use of certain plant-protection active materials, such as, for example, cymoxanil, which is unstable in alkaline medium, requires the pH of the composition to be adjusted.

In any event, the adjustment of the pH, if it is required, can be carried out using any conventional alkaline agent and in particular sodium hydroxide, potassium hydroxide, aqueous ammonia or lime.

The calcium and/or zinc and/or manganese chelates to be used according to the invention can be prepared according to general methods known to the person skilled in the art. An appropriate method consists, for example, in neutralizing the acid functional group(s) of the precursor α-hydroxycarboxylic, diphosphonic, polyphosphonic or α-hydroxyphosphonic acid or acids with one or more basic compound(s) of the abovementioned metals. Thus, for example, calcium citrate is obtained from citric acid and calcium hydroxide, which are used in solution in water in stoichiometric ratios appropriate for achieving neutrality of the suspension.

The use dose of the compositions according to the invention can vary within wide limits. It can range from 30 to 3000 g of copper per hectare but it is preferably between 300 and 3000 g of copper per hectare and, more particularly, between 500 and 2500 g.

EXAMPLES

The following examples illustrate the invention without limiting it. Except where otherwise indicated, the parts and percentages shown are expressed by weight.

Example 1

Preparation of a Calcium Citrate Precipitate 24,000 g of water and then 5043.4 g of pure citric acid monohydrate were introduced into a reactor with stirring. After complete dissolution of the citric acid, a solution of 2778.4 g of calcium hydroxide in 6000 g of water was introduced.

A calcium citrate precipitate was thus obtained, which precipitate was subsequently filtered off and dried at 75° C. The solubility in water of the final product thus obtained is 0.8 g/liter. Its calcium assay is 21%.

Example 2
Preparation of a Calcium Malate Precipitate 5000 g of water and then 4023 g of pure malic acid monohydrate were introduced into a reactor with stirring. After complete dissolution of the malic acid, a solution of 2200 g of calcium hydroxide in 2000 g of water was introduced.

A calcium malate precipitate was thus obtained, which precipitate was subsequently dried in an atomization chamber at 75° C. The solubility in water of the final product thus obtained is 3.3 g/liter.

Example 3
Preparation of a Bordeaux Mixture and Calcium Citrate Composition 57.7 parts of technical-grade Bordeaux mixture comprising 26.5% of copper ("dry BM" described in Example 1 of Patent FR 2,739,256), 6.8 parts of calcium citrate obtained according to Example 1, 7 parts of sodium lignosulphonate, 4 parts of sodium naphthalenesulphonate, 0.5 part of an antifoaming agent 2 parts of a pigment and 22 parts of kaolin were introduced into a mixer, the mixture was then milled and a wettable powder was thus obtained comprising 15% of copper, 10% of which is potentially solubilizable by the soluble citrate anions released from the calcium citrate.

Example 4
Preparation of a Bordeaux Mixture and Calcium Citrate Composition 57.5 parts of technical-grade Bordeaux mixture comprising 26.5% of copper ("dry BM" described in Example 1 of Patent FR 2,739,256), 28.8 parts of calcium citrate obtained according to Example 1, 7 parts of sodium lignosulphonate, 4 parts of sodium naphthalenesulphonate, 0.5 part of an antifoaming agent and 2 parts of a pigment were introduced into a mixer, the mixture was then milled and a wettable powder was thus obtained comprising 15% of copper, 43% of which is potentially solubilizable by the soluble citrate anions released from the calcium citrate.

Example 5
Preparation of a Bordeaux Mixture and Calcium Malate Composition 57.7 parts of technical-grade Bordeaux mixture comprising 26.5% of copper ("dry BM" described in Example 1 of Patent 2,739,256), 23.2 parts of calcium malate obtained according to Example 2, 7 parts of sodium lignosulphonate, 4 parts of sodium naphthalenesulphonate, 0.5 part of an antifoaming agent, 2 parts of a pigment and 22 parts of kaolin were introduced into a mixer, the mixture was then milled and a wettable powder was thus obtained comprising 15% of copper, 43% of which is potentially solubilizable by the soluble malate anions released from the calcium malate.

Example 6
Preparation of a Copper Hydroxide and Calcium Citrate Composition 66.7 parts of technical-grade copper hydroxide comprising 62% of copper, 18.7 parts of calcium citrate obtained according to Example 1, 7 parts of sodium lignosulphonate, 4 parts of sodium naphthalenesulphonate, 0.5 part of an antifoaming agent and 3.1 parts of kaolin were introduced into a mixer, the mixture was then milled and a wettable powder was thus obtained comprising 40% of copper, 10% of which is potentially solubilizable by the soluble citrate anions released from the calcium citrate.

Example 7
Preparation of an Aqueous Suspension Concentrate Comprising Copper Oxychloride and Calcium Citrate 204 g of sodium naphthalenesulphonate and 3.4 g of antifoaming agent were introduced, with stirring, into a reactor containing 2143 g of water. After complete dissolution, 1354 g of copper oxychloride, comprising 57% of copper, were introduced with stirring, followed, after complete dispersion, by 694 g of calcium citrate obtained according to Example 1.

After complete homogenization, an aqueous suspension was obtained assaying 250 g/liter of copper, 20% of which is potentially solubilizable by the soluble citrate anions released from the calcium citrate.

Example 8
Solubility of the Compositions According to the Invention

In order to assess the solubilities of the compositions according to the invention, the amounts of soluble copper were evaluated in vitro and compared with those obtained for the wettable powder Bordeaux mixture (WP RSR BM) described in Example 3 of Patent FR 2,739,256 and for a pure copper disodium citrate composition. The measurements were carried out after suspending the various formulations in water according to the conditions usually applied in vivo (3000 g of copper per 200 liters of water). Quantitative determination of the soluble copper was carried out after filtering at 0.45 $\mu$m.

The results are combined in the following table, the final two columns of which show, with respect to the total amount of copper, the proportion of copper solubilized after 30 minutes of equilibrium (second column) and that of chelated copper releasable subsequently (third column).

| Copper complex | % of copper solubilized after 30 minutes | % of chelated copper releasable subsequently |
| --- | --- | --- |
| Bordeaux mixture, RSR (WP) | 0.4 | 0 |
| Pure copper disodium citrate | 100 | 0 |
| Powder of Example 3 | 2.3 | 7.7 |
| Powder of Example 4 | 2.5 | 40.5 |
| Powder of Example 5 | 2.0 | 41 |
| Powder of Example 6 | 2.9 | 7.1 |

Example 9
Controlled Release of the Copper Chelate

In order to assess the control of the release, contributed by the compositions according to the invention, of the copper chelate, the amounts of copper which is solubilized in the form of copper chelate were measured as a function of the time and under conditions commonly practised in vivo (3000 g of copper per 200 liters of water).

The releases of soluble copper in the form of copper chelate were evaluated in the case of the following combinations:

$A_1$=technical-grade Bordeaux mixture comprising 26% of copper/calcium citrate $A_2$=copper oxychloride comprising 57% of copper/calcium citrate $A_3$=copper hydroxide comprising 62% of copper/calcium citrate The amount of calcium citrate was adjusted so that the total amount of copper potentially releasable from calcium citrate is 43% of the total copper content of the formula.

The results, expressed as ppm of soluble copper, are collated in the following table. By way of indication, the amount of soluble chelated copper resulting directly from a copper chelate would be 1500 ppm.

| TIME | 30 minutes | 2 hours | 24 hours |
|------|------------|---------|----------|
| A1   | 64         | 102     | 165      |
| A2   | 25         | 42      | 115      |
| A3   | 64         | 104     | 130      |

The system according to the invention makes possible, in the event of complete leaching of the soluble copper chelate present in the water at the surface of the plant, its replacement in an equivalent amount from the reservoir of citrate ions constituted by the calcium citrate precursor and from the reservoir of not very soluble copper constituted by the precursor (Bordeaux mixture, copper hydroxide, copper oxychloride and the like).

The calcium citrate used in this example had been prepared in the following way:

266 g of water and then 77.8 g of calcium hydroxide were introduced into a reactor with stirring. After homogenization of the suspension, a solution of 147.1 g of citric acid monohydrate in 266 g of water was introduced. A calcium citrate precipitate was thus obtained, which precipitate was subsequently filtered off and dried at 65° C. The final product thus obtained has a solubility in water of 1.0 g.l$^{-1}$ and its calcium, assay is 24%.

Example 10

In the context of the combating of grape downy mildew, treatment tests at reduced doses of copper per hectare were carried out with the compositions according to the invention and by comparison with Bordeaux mixture. The tests were carried out on young vine seedlings according to the CEB No. 7 method (fogging tests with artificial infection) drawn up by the Commission des Essais Biologiques de l'Association Nationale pour la Protection des Plantes [Biological Tests Commission of the National Association for the Protection of Plants]. The results of the tests are collated in the following table.

Tests at reduced doses - Preventive tests

| Composition tested | Dose of copper per hectare | % of attack |
|--------------------|---------------------------|-------------|
| None (control)     | 0 g/ha                    | 96.0        |
| Bordeaux mixture, RSR | 3000 g/ha              | 73.75       |
|                    | 2400 g/ha                 | 72.5        |
|                    | 2000 g/ha                 | 90.0        |
| Composition according to the invention: | | |
| Example 3          | 2000 g/ha                 | 81.25       |
| Example 4          | 2000 g/ha                 | 81.25       |
| Example 4          | 1500 g/ha                 | 73.75       |
| Example 5          | 2000 g/ha                 | 81.25       |

The results in the preceding table show overall that the compositions according to the invention are highly effective, even at low doses of copper per hectare. Used at a copper dose of 2000 g/ha, all the compositions according to the invention prove to be more effective than Bordeaux mixture used at the same dose. Furthermore, at a dose of 1500 g/ha, the composition of Example 4 is as effective as Bordeaux mixture used at a dose of 3000 g/ha.

Example 11

In the context of the combating of grape downy mildew, treatment tests at reduced doses of copper per hectare were carried out with a composition according to the invention and by comparison with Bordeaux mixture. These tests were carried out on according to the CEB No. 7 method; the tests are collated in the following table.

| Composition tested | Dose of Cu per hectare | Bunches of grapes 1 | 2 | 3 | 4 | Leaves 5 | 6 | 7 |
|--------------------|------------------------|---------------------|-----|------|------|----------|------|------|
| None (control)     | —                      | 100                 | 62.4 | —   | —    | 97.7     | 52.8 | —    |
| BM, RSR            | 3000                   | 19.9                | 3.13 | 72.5 | 27.6 | 57.0     | 7.9  | 9.4  |
|                    | 2400                   | 24.4                | 3.1  | 87.1 | 34.0 | 61.5     | 8.8  | 10.6 |
|                    | 1000                   | 36.8                | 6.2  | 77.7 | 31.9 | 76.2     | 14.0 | 15.6 |
| EXAMPLE 4          | 1500                   | 22.5                | 2.9  | 75.9 | 28.8 | 68       | 13.5 | 11.9 |
|                    | 1000                   | 28.9                | 6.7  | 96.1 | 40.0 | 72.5     | 15.7 | 15.6 |
|                    | 500                    | 55.8                | 14.5 | 84.9 | 51.7 | 85.7     | 23.0 | 14.9 |

1 Percentage of bunches of grapes affected after testing for 3 weeks
2 Percentage of damage to bunches of grapes after testing for 3 weeks
3 Percentage of bunches of grapes affected after testing for 10 weeks
4 Percentage of damage to bunches of grapes after testing for 10 weeks
5 Percentage of leaves affected after testing for 2 weeks
6 Percentage of damage to leaves after testing for 2 weeks
7 Overall percentage of effect on leaves after testing for 10 weeks The results in the preceding table show overall that the composition according to Example 4, used at a copper dose of 1500 g/ha, is as effective as Bordeaux mixture used at a copper dose of 3000 g/ha.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The aboves references are hereby incorporated by reference.

What is claimed is:

1. A process for producing a plant-protection composition, comprising combining a) a copper source, in non-chelated form, selected from the group consisting of a reaction product of copper sulphate and lime, copper carbonate, copper hydroxide, copper oxychloride, cuprous oxide and a copper hydroxide sulphate; and b) a chelate of an hydroxycarboxylic, diphosphonic, polyphosphonic or hydroxyphosphonic acid, and at least one member selected from the group consisting of calcium, zinc and manganese, exhibiting a solubility ranging from .001 to 50 g/l at ambient temperature, to obtain, in situ, a composition which exhibits a gradual release of copper.

2. The process according to claim 1, wherein the chelate is soluble and exhibits a solubility ranging from 0.01 to 5 g/l at ambient temperature.

3. A plant-protection composition, comprising:
a copper source, in non-chelated form, wherein the copper source is a member selected from the group consisting of a reaction product of copper sulphate and lime, copper carbonate, copper hydroxide, copper oxychloride, cuprous oxide and a copper hydroxide sulphate; and at least one chelate of a) an α-hydroxycarboxylic, diphosphonic, polyphosphonic or α-hydroxyphosphonic acid, and b) at least one member selected from the group consisting of calcium, zinc and manganese.

4. The plant-protection composition according to claim 3, wherein the composition contains a sufficient amount of the at least one calcium and/or zinc and/or manganese chelate to chelate at least a portion of the $Cu^{2+}$ ions originating from the copper source.

5. The composition according to claim 3, wherein the α-hydroxycarboxylic acid is selected from the group consisting of citric, glycolic, tartronic, gluconic, lactic, malic, tartaric and saccharic acids, the final five being in the L, D or DL form.

6. The composition according to claim 3, wherein the chelate/copper molar ratio is between 0.005 and 10.

7. The composition according to claim 3, wherein the composition is in the form of an aqueous suspension, a powder or a granule.

8. A method of effecting the plant-protection composition according to claim 3, comprising applying the composition to a plant at a dose such that the amount of copper in g/ha is between 30 and 3000.

9. The composition according to claim 6, wherein the chelate/copper molar ratio is between 0.01 and 5.

10. The composition according to claim 6, wherein the chelate/copper molar ratio is between 0.05 and 1.

11. The method according to claim 8, wherein the amount of copper in g/ha is between 300 and 3000.

12. The method according to claim 8, wherein the amount of copper in g/ha is between 500 and 2500.

13. The plant-protection composition according to claim 3, wherein the at least one chelate exhibits a solubility ranging from 0.001 to 50 g/l.

14. The plant-protection composition according to claim 3, wherein the at least one chelate exhibits a solubility ranging from 0.01 to 5 g/l.

15. A plant-protection composition, comprising:

a copper source, in non-chelated form, wherein the copper source comprises a reaction product of copper sulphate and lime in which virtually all the copper is in the brochantite state, and in which, in the dry state, not more than 20% by weight of bassanite; and at least one chelate of a) an α-hydroxycarboxylic, diphosphonic, polyphosphonic or α-hydroxyphosphonic acid, and b) at least one member selected from the group consisting of calcium, zinc and manganese.

16. A plant-protection composition, comprising:

a copper source, in non-chelated form, selected from the group consisting of a reaction product of copper sulphate and lime, copper carbonate, copper hydroxide, copper oxychloride, cuprous oxide and a copper hydroxide sulphate;

at least one chelate of a) an α-hydroxycarboxylic, diphosphonic, polyphosphonic or α-hydroxyphosphonic acid, and b) at least one member selected from the group consisting of calcium, zinc and manganese; and at least one organic fungicide.

* * * * *